(12) United States Patent
Okumura et al.

(10) Patent No.: US 8,791,307 B2
(45) Date of Patent: Jul. 29, 2014

(54) PROCESS FOR PRODUCING α,β-UNSATURATED ETHER

(75) Inventors: Yoshikuni Okumura, Minato-ku (JP);
Hiroto Kouka, Minato-ku (JP);
Takanori Aoki, Minato-ku (JP)

(73) Assignee: Showa Denko K.K., Tokyo (JP)

( * ) Notice: Subject to any disclaimer, the term of this patent is extended or adjusted under 35 U.S.C. 154(b) by 627 days.

(21) Appl. No.: 12/742,371

(22) PCT Filed: Nov. 6, 2008

(86) PCT No.: PCT/JP2008/070645
§ 371 (c)(1),
(2), (4) Date: May 11, 2010

(87) PCT Pub. No.: WO2009/063926
PCT Pub. Date: May 22, 2009

(65) Prior Publication Data
US 2010/0261936 A1    Oct. 14, 2010

(30) Foreign Application Priority Data

Nov. 13, 2007 (JP) ................................. 2007-294742

(51) Int. Cl.
*C07C 41/28* (2006.01)
*C07C 43/16* (2006.01)
*B01J 27/18* (2006.01)

(52) U.S. Cl.
USPC ............... 568/691; 502/22; 502/28; 502/324; 502/340; 502/349; 502/353

(58) Field of Classification Search
None
See application file for complete search history.

(56) References Cited

U.S. PATENT DOCUMENTS

| 1,931,858 | A | * | 10/1933 | Baur | 568/673 |
| 3,546,300 | A | * | 12/1970 | Williamson | 568/691 |
| 5,100,852 | A | | 3/1992 | Arntz et al. | |
| 5,354,911 | A | | 10/1994 | Weber et al. | |
| 5,576,465 | A | * | 11/1996 | Kaufhold | 568/691 |

FOREIGN PATENT DOCUMENTS

| EP | 1982974 A1 | 10/2008 |
| JP | 41-5376 B | 3/1966 |
| JP | 4-300845 A | 10/1992 |
| JP | 05-229977 A | 9/1993 |
| JP | 8-277237 A | 10/1996 |
| WO | 2007/086496 A1 | 8/2007 |

* cited by examiner

*Primary Examiner* — Rosalynd Keys
(74) *Attorney, Agent, or Firm* — Sughrue Mion, PLLC

(57) ABSTRACT

A process of producing α,β-unsaturated ethers includes pyrolyzing an acetal represented by Formula (2) below in a gas phase in the presence of a catalyst and a compound having at least one hydrogen atom capable of hydrogen bonding to produce an α,β-unsaturated ether represented by Formula (3) below:

$$R_1R_2CH-CR_3(OR_4)_2 \quad (2)$$

$$R_1R_2C=C-R_3(OR_4) \quad (3)$$

In Formulae (2) and (3), $R_1$, $R_2$ and $R_3$ are each independently a hydrogen atom, an alkyl group, an alkenyl group or an aryl group; $R_4$ is an alkyl group, an alkenyl group or an aryl group; the plurality of $R_4$ in Formula (2) may be the same or different from each other.

7 Claims, 3 Drawing Sheets

PROCESS FOR PRODUCING α,β-UNSATURATED ETHER

FIELD OF THE INVENTION

The present invention relates to processes for producing α,β-unsaturated ethers.

BACKGROUND OF THE INVENTION

α,β-Unsaturated ethers are homopolymerized or copolymerized with other compounds to give synthetic resins, adhesives and lubricating oils as well as intermediates for medical agents, agrichemicals and aroma chemicals, and therefore they are important materials in the industry. The α,β-unsaturated ethers are generally produced by pyrolysis of acetals. This thermal decomposition reaction usually involves a catalyst.

Patent Document 1 discloses catalysts used in the pyrolysis reaction. The catalysts disclosed are sulfates of metals having higher ionization tendency than hydrogen, or supported catalysts in which the metal sulfates are supported on solid carriers such as alumina and silica gel. The supported catalysts specifically disclosed in the document are calcium sulfate and manganese sulfate supported on alumina or magnesium silicate. They show relatively high catalytic performance in the conversion of acetal that is a starting material. However, selectivity for α,β-unsaturated ethers is often insufficient. Further, the patent document does not address the life of the catalysts.

Patent Document 2 discloses that catalyst systems containing a specific apatite achieve high catalytic activity and selectivity and have a long catalyst life. However, the document does not deal with sufficiently the regeneration of the catalysts or conventional catalysts.

Meanwhile, it is desired that catalysts in the industrial processes do not require frequent exchange to ensure productivity. In particular, the exchange frequency is desirably less than one time a year. In the pyrolysis of acetals, the high reaction temperature causes reaction such as polymerization of α,β-unsaturated ethers produced or by-product acetaldehydes, and the catalysts are quickly decayed and should be replaced frequently. Therefore, extended catalyst life is required particularly in the thermal decomposition of acetals.
Patent Document 1: JP-B-S41-5376
Patent Document 2: WO 2007/086496

DISCLOSURE OF THE INVENTION

It is an object of the invention to provide processes whereby catalysts are regenerated and used for an extended life and α,β-unsaturated ethers are produced efficiently and stably for an extended period of time.

The present inventors studied diligently to achieve the above object. They have then found that a trace amount of a compound having at least one hydrogen atom capable of hydrogen bonding can regenerate a catalyst in the pyrolysis of acetal into α,β-unsaturated ether and the catalyst can achieve a dramatically extended catalyst life. The present invention has been completed based on the finding.

The present invention relates to:

A process for producing α,β-unsaturated ethers comprising pyrolyzing an acetal in the presence of a catalyst and a compound having at least one hydrogen atom capable of hydrogen bonding.

The catalyst preferably contains an apatite represented by Formula (1) below:

$$(M)_{5-y}(HZO_4)_y(ZO_4)_{3-y}(X)_{1-y} \tag{1}$$

wherein M is at least one selected from the group consisting of Mg, Ca, Sr, Ba, Pb, Mn and Cd; Z is at least one selected from the group consisting of P, As and Sb; X is at least one selected from the group consisting of OH, F, Cl, Br, I and At; and $0 \leq y < 1$.

The apatite is preferably a calcium phosphate apatite.

The compound having at least one hydrogen atom capable of hydrogen bonding is preferably water and/or a carboxylic acid.

The concentration of water relative to the acetal is preferably 5 to 5000 ppm by weight, and the concentration of the carboxylic acid relative to the acetal is preferably 5 to 5000 ppm by weight.

The compound having at least one hydrogen atom capable of hydrogen bonding is preferably water. The concentration of water relative to the acetal is preferably 5 to 5000 ppm by weight.

Advantages of the Invention

According to the processes for producing α,β-unsaturated ethers of the invention, conventional catalyst systems are used for a dramatically extended period of time by regenerating the catalyst. As a result, the exchange frequency of the catalyst is reduced and the productivity of α,β-unsaturated ethers is improved.

PREFERRED EMBODIMENTS OF THE INVENTION

Figure 1:
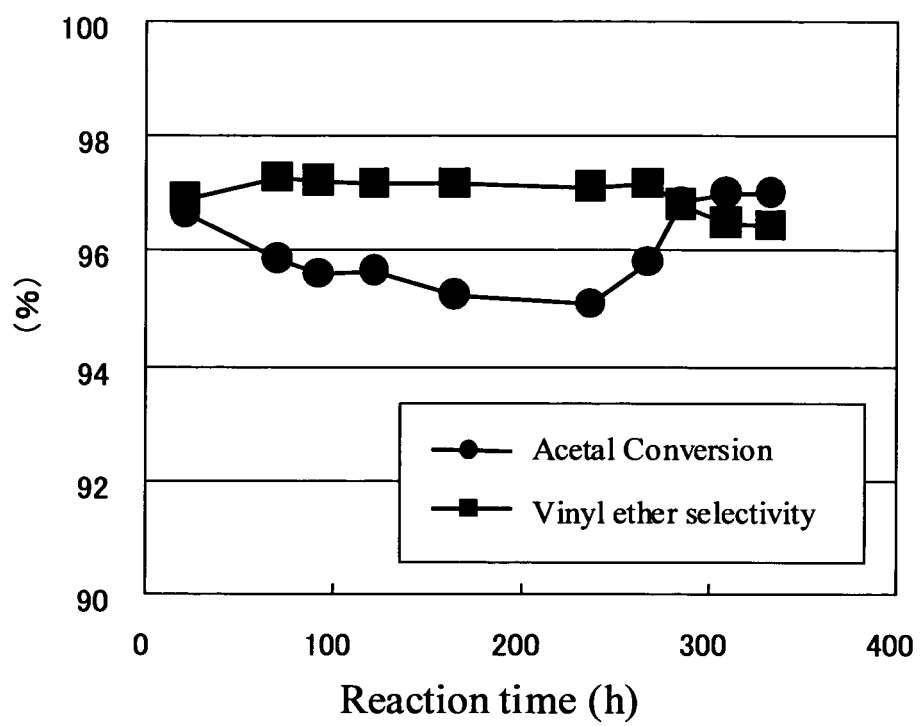
FIG. 1 shows temporal changes in acetal conversion and vinyl ether selectivity with increasing reaction time in Example 9.

The processes for producing α,β-unsaturated ethers according to the present invention will be described hereinbelow.

In the process for producing α,β-unsaturated ethers, an acetal is pyrolyzed in the presence of a catalyst and a compound having at least one hydrogen atom capable of hydrogen bonding. The acetals used herein include those derived from aldehydes and those from ketones, namely, ketals. The compounds having at least one hydrogen atom capable of hydrogen bonding are compounds that have at least one X—H bonding (wherein X is a highly electronegative atom such as O, N or S) in the molecule.

In the process of producing α,β-unsaturated ethers, an acetal represented by Formula (2) below is pyrolyzed in a gas phase in the presence of a catalyst and a compound having at least one hydrogen atom capable of hydrogen bonding to produce an α,β-unsaturated ether represented by Formula (3) below:

$$R_1R_2CH-CR_3(OR_4)_2 \tag{2}$$

$$R_1R_2C=C-R_3(OR_4) \tag{3}$$

In Formulae (2) and (3), $R_1$, $R_2$ and $R_3$ are each independently a hydrogen atom, an alkyl group, an alkenyl group or an aryl group; $R_4$ is an alkyl group, an alkenyl group or an aryl group; the plurality of $R_4$ in Formula (2) may be the same or different from each other.

<Acetals>

The acetals that are reaction materials in the invention include acetaldehyde dimethyl acetal, acetaldehyde diethyl acetal, acetaldehyde di-n-propyl acetal, acetaldehyde di-n-butyl acetal, acetaldehyde diisobutyl acetal, acetaldehyde dibenzyl acetal, propionaldehyde diethyl acetal, butylaldehyde diethyl acetal, 2,2-dimethoxypropane, 2,2-diethoxypropane and 2,2-dibenzylpropane.

<Compounds Having at Least One Hydrogen Atom Capable of Hydrogen Bonding>

Examples of the compounds having at least one hydrogen atom capable of hydrogen bonding include water, alcohols, carboxylic acids, amines, amides and thiols. Of these, water and carboxylic acids are preferable.

The water is not particularly limited. To eliminate influences by impurities, water purified by ion exchange or distillation is preferable.

The carboxylic acids are represented by RCOOH, and may be monocarboxylic acids with one carboxyl group, dicarboxylic acids with two carboxylic groups, or tricarboxylic acids with three carboxyl groups. Examples of the carboxylic acids include formic acid, acetic acid, propionic acid, butyric acid, crotonic acid, benzoic acid, lactic acid, oxalic acid, malonic acid, succinic acid, phthalic acid, maleic acid, fumaric acid, glutaric acid and adipic acid. Of these, formic acid, acetic acid, propionic acid and crotonic acid are preferable. The carboxylic acids may be used singly, or two or more kinds may be used in combination.

The compounds having at least one hydrogen atom capable of hydrogen bonding may be used singly, or two or more kinds may be used in combination. Different kinds of the compounds having at least one hydrogen atom capable of hydrogen bonding, for example water and carboxylic acids, may be used in combination.

When water is used as the compound having at least one hydrogen atom capable of hydrogen bonding, the concentration of water relative to the acetal is generally 5 to 5000 ppm by weight, and preferably 5 to 1500 ppm by weight. If the water concentration is less than this range, it is likely that the catalyst life is not extended. If the water concentration exceeds the above range, more aldehydes are by-produced and the selectivity for $\alpha,\beta$-unsaturated ethers is lowered. Further, it is likely that the by-product aldehydes cause coking and deteriorate the catalyst to reduce the catalyst life.

When the carboxylic acid is used as the compound having at least one hydrogen atom capable of hydrogen bonding, the concentration of the carboxylic acid relative to the acetal is generally 5 to 5000 ppm by weight, and preferably 5 to 1500 ppm by weight. If the carboxylic acid concentration is less than this range, it is likely that the catalyst life is not extended.

<Catalysts>

The catalysts used in the invention are not particularly limited. Examples include oxides such as apatites, alumina, silica gel, zeolites, clay minerals, activated carbon, silica-magnesia, magnesium oxide, lithium oxide, zinc oxide and titanium oxide; sulfates, carbonates, phosphates, molybdates and nitrates of metals having higher ionization tendency than hydrogen; and supported catalysts in which the above metal salts are supported on solid carriers such as alumina and silica gel.

Of the catalysts, a particularly preferred catalyst contains an apatite represented by Formula (1) below:

$$(M)_{5-y}(HZO_4)_y(ZO_4)_{3-y}(X)_{1-y} \quad (1)$$

wherein M is at least one selected from the group consisting of Mg, Ca, Sr, Ba, Pb, Mn and Cd; Z is at least one selected from the group consisting of P, As and Sb; X is at least one selected from the group consisting of OH, F, Cl, Br, I and At; and $0 \leq y < 1$.

Apatites are otherwise called phosphate minerals and have a general composition represented by Formula (1): $(M)_{5-y}(HZO_4)_y(ZO_4)_{3-y}(X)_{1-y}$. The apatites refer to compounds belonging to hexagonal crystals $P6_{3/m}$, or monoclinic crystals $P2_{1/b}$. When y in the general formula is 0, the compounds are represented by $M_5(ZO_4)_3(X)$, called the stoichiometric apatites. When $0 < y < 1$, the compounds are nonstoichiometric apatites.

Examples of the apatites include phosphates (Z=P), arsenic salts (Z=As) and antimonates (Z=Sb), with phosphates being particularly preferred.

In the stoichiometric phosphate apatites $M_5(PO_4)_3(X)$, X is preferably OH, F or Cl. Specific examples include hydroxyapatites $M_5(PO_4)_3OH$, fluoroapatites $M_5(PO_4)_3(F)$ and chloroapatites $M_5(PO_4)_3(Cl)$. These hydroxyphosphate apatites, fluorophosphate apatites and chlorophosphate apatites may be pure apatites without any other components, or may contain OH, F and Cl at any ratio.

The hydroxyapatites include magnesium salt $Mg_5(PO_4)_3(OH)$, calcium salt $Ca_5(PO_4)_3(OH)$, strontium salt $Sr_5(PO_4)_3(OH)$, barium salt $Ba_5(PO_4)_3(OH)$, manganese salt $Mn_5(PO_4)_3(OH)$ and lead salt $Pb_5(PO_4)_3(OH)$. Composites of these salts may be used.

The fluoroapatites include magnesium salt $Mg_5(PO_4)_3(F)$, calcium salt $Ca_5(PO_4)_3(F)$, strontium salt $Sr_5(PO_4)_3(F)$, barium salt $Ba_5(PO_4)_3(F)$, manganese salt $Mn_5(PO_4)_3(F)$ and lead salt $Pb_5(PO_4)_3(F)$. Composites of these salts may be used.

The chloroapatites include magnesium salt $Mg_5(PO_4)_3(Cl)$, calcium salt $Ca_5(PO_4)_3(Cl)$, strontium salt $Sr_5(PO_4)_3(Cl)$, barium salt $Ba_5(PO_4)_3(Cl)$, manganese salt $Mn_5(PO_4)_3(Cl)$ and lead salt $Pb_5(PO_4)_3(Cl)$. Composites of these salts may be used.

Of the catalysts, those based on magnesium phosphate apatite, calcium phosphate apatite, strontium phosphate apatite or barium phosphate apatite are preferable. In particular, calcium phosphate apatite is preferably used in the processes for producing $\alpha,\beta$-unsaturated ethers.

In the production of $\alpha,\beta$-unsaturated ethers according to the present invention, the catalyst life is drastically extended by using the conventional catalyst together with the compounds having at least one hydrogen atom capable of hydrogen bonding. Consequently, the exchange frequency of the catalyst is reduced and the productivity of $\alpha,\beta$-unsaturated ethers is enhanced.

<$\alpha,\beta$-Unsaturated Ethers>

The $\alpha,\beta$-unsaturated ethers produced in the invention are represented by Formula (3) described above. Examples thereof include methyl vinyl ether, ethyl vinyl ether, n-propyl vinyl ether, n-butyl vinyl ether, isobutyl vinyl ether, benzyl vinyl ether, 2-methoxy-1-propene, 2-ethoxy-1-propene, 2-propoxy-1-propene and 2-butoxy-1-propene.

<Conditions in Production of $\alpha,\beta$-Unsaturated Ethers>

In the production of $\alpha,\beta$-unsaturated ethers, a fixed-bed or fluidized-bed gas phase flow reactor may be used. For example, satisfactory results are obtained by using a gas phase flow reactor that is equipped with a fixed bed formed of 10-20 mesh catalyst particles. The fixed bed reactor may be a vertical or horizontal tube.

In the invention, the compounds having at least one hydrogen atom capable of hydrogen bonding may be supplied to the acetal by any method without limitation. For example, the acetal and the compound having at least one hydrogen atom capable of hydrogen bonding may be mixed beforehand and supplied to the reactor together. Alternatively, the compound having at least one hydrogen atom capable of hydrogen bonding may be supplied to an acetal supply line. Still alternatively, the compound having at least one hydrogen atom capable of hydrogen bonding may be supplied to the reactor through a supply line separate from the acetal supply line. The compound having at least one hydrogen atom capable of hydrogen bonding may be fed to the reaction in the form of a solution in a solvent. The solvents used herein may be conventional as long as the solvents are inert under reaction conditions. Exemplary solvents include aliphatic solvents such as hexane and heptane; and aromatic solvents such as benzene, toluene and xylene.

The temperature in the gas-phase pyrolysis of acetal may vary depending on the type of the acetal or the contact time with the catalyst, but is generally in the range of 150 to 400° C., and preferably 200 to 380° C. The lower limit of pyrolysis temperature in the above range ensures that the equilibrium reaction provides a high acetal conversion. The upper limit ensures that the pyrolysis is not substantially accompanied by side reactions and cokes are not precipitated. The reaction may be carried out continuously by successively supplying the acetal while the reaction temperature is maintained in the above range. In the reaction, it is preferable that the acetal is preheated.

The pyrolysis reaction may be performed at atmospheric pressure, reduced pressure or increased pressure.

The objective α,β-unsaturated ether may be separated from the pyrolysis product resulting from the catalytic cracking by fractional distillation of the gaseous mixture discharged from the reactor.

EXAMPLES

Preferred embodiments of the present invention will be described below by presenting Examples without limiting the scope of the invention.

The acetal conversion and vinyl ether selectivity in Examples are defined by the following equations:

Acetal conversion(%)=[(moles of acetal reacted)/ (moles of acetal supplied to reaction)]×100

Vinyl ether selectivity(%)=[(moles of vinyl ether produced)/(moles of acetal reacted)]×100

Properties were measured as follows.
<Analysis of Water Concentration Relative to Acetal (Karl Fischer Method)>
The water concentration relative to acetal was determined by Karl Fischer method under the following conditions. The detection limit was 2 ppm by weight.
Measurement sample: 1 ml
Anode solution: Riedel-de Haen Hydramal-Coulomat AK (for ketone analysis)
Cathode solution: Riedel-de Haen Hydramal-Coulomat CG-K
<Analysis of Acid Concentration Relative to Acetal (Anion Chromatography)>
The acid concentration relative to acetal was determined by anion chromatography under the following conditions. The detection limit was 2 ppm by weight.
Chromatograph: DIONEX DX-500
Separation column: Shodex IC SI-90 4E (room temperature)
Eluting solution: $Na_2CO_3$ (1.8 mM)+$NaHCO_3$ (1.7 mM)
Flow rate: 1.0 ml/min
Injection amount: 25 μl
Detector: Electrical conductivity detector
Suppressor: ASRS-ULTRA II (recycle mode)

Example 1

Preparation of Catalyst 10 g of hydroxyapatite $Ca_5(PO_4)_3(OH)$ (manufactured by Wako Pure Chemical Industries, Ltd.) was pressure molded at 20 MPa for 5 minutes, and the particles formed were sieved to sizes from 0.85 to 1.70 mm in diameter. The particles were then placed in a calcination tube and were calcined at 350° C. under atmospheric pressure in a nitrogen atmosphere for 3 hours. The particles were cooled to room temperature in 1 hour while nitrogen was continuously flowed. A catalyst was thus obtained.
Preparation of Material:
500 ml of acetaldehyde diethyl acetal was given 170 g of molecular sieve 4A (1/16 inch diameter cylinder) and was allowed to stand still for 12 hours. The resultant dehydrated acetaldehyde diethyl acetal weighing 90 g was separated from the molecular sieve by decantation, and 0.063 g of acetic acid was added thereto. The water concentration and acetic acid concentration in the acetaldehyde diethyl acetal solution were determined to be 40 ppm and 700 ppm by weight, respectively, relative to the acetal.
Reaction Experiment:
1 ml of the catalyst prepared as described above was placed in a stainless steel reaction tube (diameter: 12.7 mm, length: 300 mm). To the reaction tube, the acetaldehyde diethyl acetal solution was fed at 15 g/h (corresponding to SV3000/h). The solution was evaporated at 250° C. and reaction was carried out at 360° C. under atmospheric pressure.

After 6 hours from the reaction initiation, the reaction solution obtained was analyzed by gas chromatography, confirming ethyl vinyl ether as a main product. The acetal conversion was 86.5% and the vinyl ether selectivity was 98.6%. The results are shown in Table 1.

Example 2

Preparation of Material

A material was prepared in the same manner as in Example 1 except that acetic acid was added in an amount of 0.253 g. The water concentration and acetic acid concentration in the acetaldehyde diethyl acetal solution were determined to be 40 ppm and 2808 ppm by weight, respectively, relative to the acetal.
Reaction Experiment:
Reaction was performed in the same manner as in Example 1. After 6 hours from the reaction initiation, the reaction solution obtained was analyzed by gas chromatography, confirming ethyl vinyl ether as a main product. The acetal conversion was 92.0% and the vinyl ether selectivity was 99.0%. The results are shown in Table 1.

Comparative Example 1

Preparation of Material

A material was prepared in the same manner as in Example 1 except that acetic acid was not added. The water concentration and acetic acid concentration in the acetaldehyde diethyl acetal solution were both determined to be below the detection limit (below 2 ppm by weight) relative to the acetal.

Reaction Experiment:

Reaction was performed in the same manner as in Example 1. After 6 hours from the reaction initiation, the reaction solution obtained was analyzed by gas chromatography, confirming ethyl vinyl ether as a main product. The acetal conversion was 74.5% and the vinyl ether selectivity was 98.5%. The results are shown in Table 1.

Example 3

Preparation of Material

A material was prepared in the same manner as in Example 1 except that 0.324 g of water was added instead of acetic acid. The water concentration and acetic acid concentration in the acetaldehyde diethyl acetal solution were determined to be 3613 ppm by weight and below the detection limit (below 2 ppm by weight), respectively, relative to the acetal.

Reaction Experiment:

Reaction was performed in the same manner as in Example 1. After 6 hours from the reaction initiation, the reaction solution obtained was analyzed by gas chromatography, confirming ethyl vinyl ether as a main product. The acetal conversion was 78.9% and the vinyl ether selectivity was 95.5%. The results are shown in Table 1.

Example 4

Preparation of Material

A material was prepared in the same manner as in Example 1 except that 0.117 g of water was added together with 0.063 g of acetic acid. The water concentration and acetic acid concentration in the acetaldehyde diethyl acetal solution were determined to be 1302 ppm and 700 ppm by weight, respectively, relative to the acetal.

Reaction Experiment:

Reaction was performed in the same manner as in Example 1. After 6 hours from the reaction initiation, the reaction solution obtained was analyzed by gas chromatography, confirming ethyl vinyl ether as a main product. The acetal conversion was 88.0% and the vinyl ether selectivity was 98.2%. The results are shown in Table 1.

Example 5

Preparation of Material

A material was prepared in the same manner as in Example 4 except that 0.063 g of acetic acid and 0.324 g of water were added. The water concentration and acetic acid concentration in the acetaldehyde diethyl acetal solution were determined to be 3613 ppm and 700 ppm by weight, respectively, relative to the acetal.

Reaction Experiment:

Reaction was performed in the same manner as in Example 1. After 6 hours from the reaction initiation, the reaction solution obtained was analyzed by gas chromatography, confirming ethyl vinyl ether as a main product. The acetal conversion was 89.2% and the vinyl ether selectivity was 96.1%. The results are shown in Table 1.

Example 6

Preparation of Material

A material was prepared in the same manner as in Example 4 except that 0.253 g of acetic acid and 0.117 g of water were added. The water concentration and acetic acid concentration in the acetaldehyde diethyl acetal solution were determined to be 1302 ppm and 2808 ppm by weight, respectively, relative to the acetal.

Reaction Experiment:

Reaction was performed in the same manner as in Example 1. After 6 hours from the reaction initiation, the reaction solution obtained was analyzed by gas chromatography, confirming ethyl vinyl ether as a main product. The acetal conversion was 92.4% and the vinyl ether selectivity was 96.1%. The results are shown in Table 1.

TABLE 1

| | Water concentration (ppm by weight) | Acetic acid concentration (ppm by weight) | Acetal conversion (%) | Vinyl ether selectivity (%) |
|---|---|---|---|---|
| Ex. 1 | 40 | 700 | 86.5 | 98.6 |
| Ex. 2 | 40 | 2808 | 92.0 | 99.0 |
| Comp. Ex. 1 | Below detection limit | Below detection limit | 74.5 | 98.5 |
| Ex. 3 | 3613 | Below detection limit | 78.9 | 95.5 |
| Ex. 4 | 1302 | 700 | 88.0 | 98.2 |
| Ex. 5 | 3613 | 700 | 89.2 | 96.1 |
| Ex. 6 | 1302 | 2808 | 92.4 | 96.1 |

Example 7

Preparation of Material

A material was prepared in the same manner as in Example 1 except that 0.05 g of formic acid was added instead of acetic acid. The water concentration and formic acid concentration in the acetaldehyde diethyl acetal solution were determined to be 40 ppm and 550 ppm by weight, respectively, relative to the acetal.

Reaction Experiment:

Reaction was performed in the same manner as in Example 1. After 6 hours from the reaction initiation, the reaction solution obtained was analyzed by gas chromatography, confirming ethyl vinyl ether as a main product. The acetal conversion was 82.3% and the vinyl ether selectivity was 98.6%. The results are shown in Table 2.

Example 8

Preparation of Material

A material was prepared in the same manner as in Example 1 except that 0.09 g of crotonic acid was added instead of acetic acid. The water concentration and crotonic acid concentration in the acetaldehyde diethyl acetal solution were determined to be 40 ppm and 1000 ppm by weight, respectively, relative to the acetal.

Reaction Experiment:

Reaction was performed in the same manner as in Example 1. After 6 hours from the reaction initiation, the reaction solution obtained was analyzed by gas chromatography, confirming ethyl vinyl ether as a main product. The acetal conversion was 88.9% and the vinyl ether selectivity was 96.1%. The results are shown in Table 2.

TABLE 2

| | Water concentration (ppm by weight) | Carboxylic acid concentration (ppm by weight) | Acetal conversion (%) | Vinyl ether selectivity (%) |
|---|---|---|---|---|
| Ex. 7 | 40 | Formic acid 550 | 82.3 | 98.6 |
| Ex. 8 | 40 | Crotonic acid 1000 | 88.9 | 96.1 |

Example 9

Reaction Experiment 2 ml of the catalyst prepared in Example 1 was placed in a stainless steel reaction tube (diameter: 12.7 mm, length: 300 mm). To the reaction tube, an acetaldehyde diethyl acetal solution in which the water concentration and acetic acid concentration relative to the acetal were both adjusted to below the detection limit (below 2 ppm by weight) was fed at 11 g/h. The solution was evaporated at 250° C. and reaction was carried out at an electric furnace temperature of 315° C. under atmospheric pressure (corresponding to SV1040/h).

The reaction solution was analyzed with the passage of time from the reaction initiation. After 238 hours from the reaction initiation, the material solution was changed to an acetaldehyde diethyl acetal solution in which the water concentration and acetic acid concentration relative to the acetal were adjusted to 1302 ppm and 700 ppm by weight, respectively. The reaction solution was analyzed with the passage of time thereafter. The results of time-series analysis are set forth in Table 3 and FIG. 1.

Table 3 and FIG. 1 demonstrate that the acetal conversion gradually lowered in the case of the acetaldehyde diethyl acetal solution in which the water concentration and acetic acid concentration relative to the acetal were both adjusted to below the detection limit (below 2 ppm by weight), whereas the acetal conversion increased without showing any lowering tendency after the material solution was changed to the acetaldehyde diethyl acetal solution in which the water concentration and acetic acid concentration relative to the acetal were adjusted to 1302 ppm and 700 ppm by weight, respectively. This result indicates that the acetaldehyde diethyl acetal solution in which the water concentration and acetic acid concentration relative to the acetal were adjusted to 1302 ppm and 700 ppm by weight, respectively, regenerated the catalyst to extend the catalyst life and prevented lowering in catalytic performance.

TABLE 3

| Water concentration (ppm by weight) | Acetic acid concentration (ppm by weight) | Reaction time (h) | Acetal conversion (%) | Vinyl ether selectivity (%) |
|---|---|---|---|---|
| Below detection limit | Below detection limit | 20 | 96.7 | 96.9 |
| | | 70 | 95.9 | 97.3 |
| | | 93 | 95.6 | 97.2 |
| | | 123 | 95.7 | 97.2 |
| | | 166 | 95.2 | 97.2 |
| | | 238 | 95.1 | 97.1 |
| 1302 | 700 | 267 | 95.8 | 97.2 |
| | | 285 | 96.8 | 96.8 |
| | | 309 | 97.0 | 96.5 |
| | | 333 | 97.0 | 96.4 |

Example 10

Reaction Experiment

Reaction was carried out in the same manner as in Example 9 using an acetaldehyde diethyl acetal solution in which the water concentration and acetic acid concentration relative to the acetal were both adjusted to below the detection limit (below 2 ppm by weight). The reaction solution was analyzed with the passage of time. After 170 hours from the reaction initiation, the material solution was changed to an acetaldehyde diethyl acetal solution in which the water concentration and acetic acid concentration relative to the acetal were adjusted to 320 ppm by weight and below the detection limit (below 2 ppm by weight), respectively. The reaction solution was analyzed with the passage of time thereafter. The results of time-series analysis are set forth in Table 4 and FIG. 2.

Figure 2:
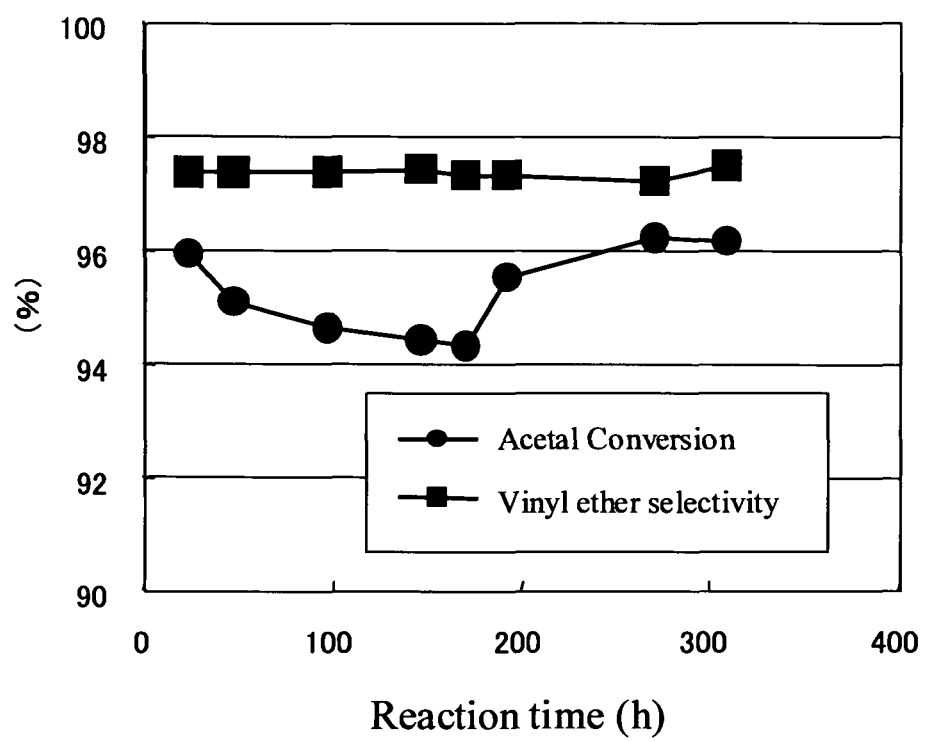
FIG. 2 shows temporal changes in acetal conversion and vinyl ether selectivity with increasing reaction time in Example 10.

Table 4 and FIG. 2 demonstrate that the acetal conversion gradually lowered in the case of the acetaldehyde diethyl acetal solution in which the water concentration and acetic acid concentration relative to the acetal were both adjusted to below the detection limit (below 2 ppm by weight), whereas the acetal conversion increased without showing any lowering tendency after the material solution was changed to the acetaldehyde diethyl acetal solution in which the water concentration and acetic acid concentration relative to the acetal were adjusted to 320 ppm by weight and below the detection limit (below 2 ppm by weight), respectively. This result indicates that the acetaldehyde diethyl acetal solution in which the water concentration and acetic acid concentration relative to the acetal were adjusted to 320 ppm by weight and below the detection limit (below 2 ppm by weight), respectively, regenerated the catalyst to extend the catalyst life and prevented lowering in catalytic performance.

TABLE 4

| Water concentration (ppm by weight) | Acetic acid concentration (ppm by weight) | Reaction time (h) | Acetal conversion (%) | Vinyl ether selectivity (%) |
|---|---|---|---|---|
| Below detection limit | Below detection limit | 24 | 96.0 | 97.4 |
| | | 48 | 95.1 | 97.4 |
| | | 97 | 94.6 | 97.4 |
| | | 146 | 94.4 | 97.4 |
| | | 170 | 94.3 | 97.3 |
| 320 | Below detection limit | 192 | 95.5 | 97.3 |
| | | 272 | 96.2 | 97.2 |
| | | 310 | 96.2 | 97.5 |

Example 11

Reaction Experiment

Reaction was carried out in the same manner as in Example 9 using an acetaldehyde diethyl acetal solution in which the water concentration and acetic acid concentration relative to the acetal were both adjusted to below the detection limit (below 2 ppm by weight). The reaction solution was analyzed with the passage of time. After 145 hours from the reaction initiation, the material solution was changed to an acetaldehyde diethyl acetal solution in which the water concentration and acetic acid concentration relative to the acetal were adjusted to 40 ppm and 250 ppm by weight, respectively. The reaction solution was analyzed with the passage of time thereafter. After 313 hours from the reaction initiation, the material solution was changed to an acetaldehyde diethyl acetal solution in which the water concentration and acetic acid concentration relative to the acetal were both adjusted to below the detection limit (below 2 ppm by weight). After 361 hours from the reaction initiation, the material solution was changed to an acetaldehyde diethyl acetal solution in which the water concentration and acetic acid concentration relative to the acetal were adjusted to 40 ppm by weight and below the detection limit (below 2 ppm by weight), respectively. The reaction solution was analyzed with the passage of time thereafter. The results of time-series analysis are set forth in Table 5 and FIG. 3.

Figure 3:
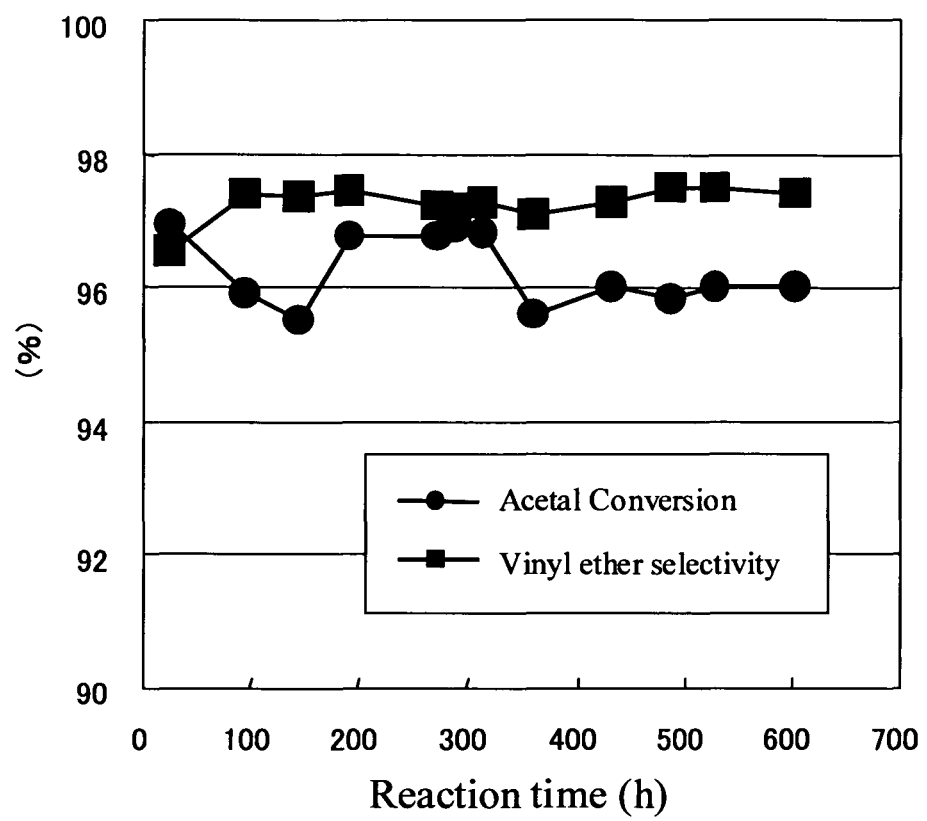
FIG. 3 shows temporal changes in acetal conversion and vinyl ether selectivity with increasing reaction time in Example 11.

Table 5 and FIG. 3 demonstrate that the acetal conversion lowered in the case of the acetaldehyde diethyl acetal solution in which the water concentration and acetic acid concentration relative to the acetal were both adjusted to below the detection limit (below 2 ppm by weight), whereas the acetal conversion increased after the material solution was changed to the acetaldehyde diethyl acetal solution in which the water concentration and acetic acid concentration relative to the acetal were adjusted to 40 ppm and 250 ppm by weight, respectively. The acetal conversion started to decrease again after the material solution was changed to the acetaldehyde diethyl acetal solution in which the water concentration and acetic acid concentration relative to the acetal were both adjusted to below the detection limit (below 2 ppm by weight). However, the acetal conversion ceased to decrease after the material solution was changed to the acetaldehyde diethyl acetal solution in which the water concentration and acetic acid concentration relative to the acetal were adjusted to 40 ppm by weight and below the detection limit (below 2 ppm by weight), respectively.

TABLE 5

| Water concentration (ppm by weight) | Acetic acid concentration (ppm by weight) | Reaction time (h) | Acetal conversion (%) | Vinyl ether selectivity (%) |
| --- | --- | --- | --- | --- |
| Below detection limit | Below detection limit | 24 | 96.9 | 96.6 |
|  |  | 95 | 95.9 | 97.4 |
|  |  | 145 | 95.5 | 97.4 |
| 40 | 250 | 192 | 96.8 | 97.4 |
|  |  | 271 | 96.8 | 97.2 |
|  |  | 288 | 96.9 | 97.2 |
|  |  | 313 | 96.8 | 97.2 |
| Below detection limit | Below detection limit | 361 | 95.6 | 97.1 |
| 40 | Below detection limit | 433 | 96.0 | 97.3 |
|  |  | 486 | 95.8 | 97.5 |
|  |  | 528 | 96.0 | 97.5 |
|  |  | 604 | 96.0 | 97.4 |

The invention claimed is:

1. A process for producing α,β-unsaturated ethers, comprising pyrolyzing an acetal in a gas phase in the presence of a catalyst and a compound having at least one hydrogen atom capable of hydrogen bonding,
wherein the compound having at least one hydrogen atom capable of hydrogen bonding is water and/or a carboxylic acid;
wherein the process comprises:
a step of supplying the water and optionally the carboxylic acid to the acetal to obtain an acetal solution, wherein the concentration of the water relative to the acetal is 40 to 5000 ppm by weight when supplying the water, and the concentration of the carboxylic acid relative to the acetal is 5 to 5000 ppm by weight when supplying the carboxylic acid, and
a step of feeding the acetal solution to a reactor with the catalyst;
wherein the catalyst contains an apatite represented by Formula (1) below:

$$(M)_{5-y}(HZO_4)_y(ZO_4)_{3-y}(X)_{1-y} \qquad (1)$$

wherein M is at least one selected from the group consisting of Mg, Ca, Sr, Ba, Pb, Mn and Cd; Z is at least one selected from the group consisting of P, As and Sb; X is at least one selected from the group consisting of OH, F, Cl, Br, I and At; and $0 \leq y < 1$;
wherein the temperature in the gas-phase pyrolysis of the acetal is in the range of 150 to 400° C.

2. The process according to claim 1, wherein the apatite is a calcium phosphate apatite.

3. The process according to claim 1, wherein the concentration of water relative to the acetal is 40 to 3613 ppm by weight, and the concentration of the carboxylic acid relative to the acetal is 5 to 5000 ppm by weight.

4. The process according to any one of claims 1 and 2, wherein the compound having at least one hydrogen atom capable of hydrogen bonding is water.

5. The process according to claim 4, wherein the concentration of water relative to the acetal is 40 to 1500 ppm by weight.

6. The process according to claim 1, wherein
(i) the acetal and the compound having at least one hydrogen atom capable of hydrogen bonding are mixed beforehand and supplied to a reactor together; or
(ii) the compound having at least one hydrogen atom capable of hydrogen bonding is supplied to an acetal supply line.

7. The process according to claim 1, wherein the process comprises a step of supplying the water to the acetal to obtain an acetal solution, wherein the concentration of the water relative to the acetal is 40 to 3613 ppm by weight, and a step of feeding the acetal solution to a reactor with the catalyst.

* * * * *